United States Patent [19]

Nishida et al.

[11] Patent Number: 4,742,074

[45] Date of Patent: May 3, 1988

[54] PYRAZOLECARBOXAMIDE DERIVATIVE AND FUNGICIDE CONTAINING IT AS ACTIVE INGREDIENT

[75] Inventors: Sumio Nishida, Takarazuka; Tadashi Ohsumi; Kazunori Tsushima, both of Nishinomiya, all of Japan; Noritada Matsuo, Rochester, N.Y.; Kiyoto Maeda, Nishinomiya, Japan; Satoru Inoue, Clevedon, United Kingdom

[73] Assignee: Sumitomo Chemical Company, Limited, Osaka, Japan

[21] Appl. No.: 852,967

[22] PCT Filed: Oct. 22, 1985

[86] PCT No.: PCT/JP85/00591

§ 371 Date: Mar. 31, 1986

§ 102(e) Date: Mar. 31, 1986

[87] PCT Pub. No.: WO86/02641

PCT Pub. Date: May 9, 1986

[30] Foreign Application Priority Data

Jun. 5, 1985 [JP] Japan .................................. 60-121947
Jul. 8, 1985 [JP] Japan .................................. 60-150935
Oct. 29, 1985 [JP] Japan .................................. 59-227462

[51] Int. Cl.[4] .................. A01N 43/56; C07D 231/14; C07D 231/16

[52] U.S. Cl. .................................. 514/406; 548/376; 548/377; 548/378

[58] Field of Search .................. 548/376, 377, 378; 514/406

[56] References Cited

U.S. PATENT DOCUMENTS 4,134,987 1/1979 Huppatz .............................. 548/378
4,460,603 7/1984 Chan .................................. 548/378

FOREIGN PATENT DOCUMENTS 49-116062 6/1974 Japan .................................. 548/378
60-34949 2/1985 Japan .................................. 548/378

Primary Examiner—Henry R. Jiles
Assistant Examiner—Kurt G. Briscoe
Attorney, Agent, or Firm—Ladas & Parry

[57] ABSTRACT

A pyrazolecarboxamide derivative represented by the formula hereinbelow is useful since it has preventively, curatively or systematically controlling effects against various plant diseases and fungicides containing said compound as an active ingredient have excellent controlling activities:

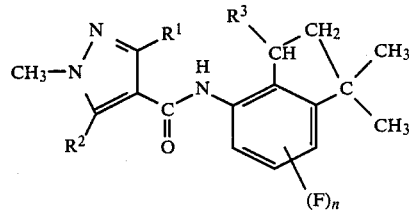

wherein $R^1$ and $R^2$ which are identical or different and represent each a hydrogen atom, a halogen atom, a methyl group, an ethyl group or a trifluoromethyl group, $R^3$ represents a hydrogen atom or a methyl group and n represents 0 or 1.

15 Claims, No Drawings

PYRAZOLECARBOXAMIDE DERIVATIVE AND FUNGICIDE CONTAINING IT AS ACTIVE INGREDIENT

The present invention relates to a pyrazolecarboxamide derivative (referred to as "present compound" hereinafter) represented by the formula

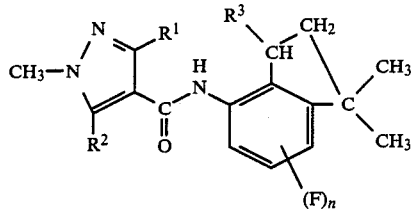

wherein $R^1$ and $R^2$ which are identical or different and represent a hydrogen atom, a halogen atom, a methyl group, an ethyl group or a trifluoromethyl group, $R^3$ represents a hydrogen atom or a methyl group and n represents 0 or 1, and a method for preparing the same and a fungicide containing the derivative as an active ingredient.

The inventors have made extensive research on pyrazolecarboxamide compounds and as a result, have found that the present compound represented by the formula [I] has preventive, curative and systemic controlling effects on plant microbes. The present invention is based on this finding.

The following are plant diseases on which the present compound has an excellent controlling effect; *Rhizoctonia solani* and *Rhizoctonia oryzae*, *R. solani* III B on rice plant; *Puccinia striiformis*, *P. graminis*, *P. recondita*, *P. hordei*, *Rhizoctonia cerealis*, *Typhula incarnata*, *T. ishikariensis*, *Ustilago tritici* and *U. nuda* on wheat; *Rhizoctonia solani* and *Corticium rolfsii* on various crops; *Rhizoctonia solani* on potato and beet; *Gymnosporangium haraeanum* on pear; *Venturia inaequaris* on apple; *Rhizoctonia solani*, *Corticium rolfsii*, *Uromyces trifolii* and *Typhula incarnata*, *T. ishikariensis* on pasture and lawn.

The present compound can be produced, for example, by the following methods.

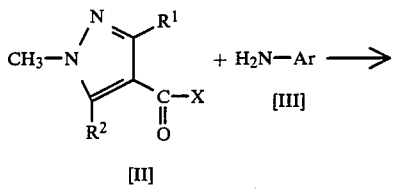

[Method A]

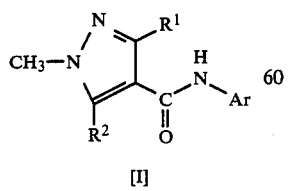

wherein $R^1$, $R^2$, $R^3$ and n are as defined above, X represents a halogen atom and Ar represents a group having the formula:

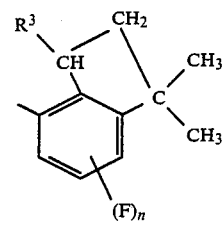

(wherein $R^3$ and n are as defined above).

That is, a carboxylic acid halide represented by the formula [II], e.g., carboxylic acid chloride, carboxylic acid bromide and carboxylic acid fluoride, is reacted with a 4-aminoindane derivative represented by the formula [III] to obtain the present compound represented by the formula [I].

Reaction solvents are not essential for the above method, but generally inert solvents are used. As examples of the solvents, the following may be listed; hydrocarbons such as benzene, toluene, xylene, etc., halogenated hydrocarbons such as chloroform, dichloromethane, chlorobenzene, etc., ethers such as diethyl ether, diisopropyl ether, tetrahydrofuran, dioxane, dimethoxyethane, etc., ketones such as acetone, methyl isobutyl ketone, etc., esters such as ethyl acetate, etc., nitriles such as acetonitrile, etc., dimethylsulfoxide, sulfolane, dimethylformamide, dimethylacetamide, etc. and mixtures thereof.

The reaction may be carried out in the presence of an acid accepting agent. Examples of the acid accepting agent are organic bases such as triethylamine, pyridine, N,N-dimethylaniline, 4-dimethylaminopyridine, etc. and inorganic bases such as sodium carbonate, potassium carbonate, sodium hydroxide, potassium hydroxide, etc.

Reaction temperature has no special limitation, but usually is 0° C.–150° C.

Amount of the starting compounds used in this reaction is generally 0.8–1.5 mol of the 4-aminoindane derivative represented by the formula [III] per 1 mol of the carboxylic acid halide represented by the formula [II].

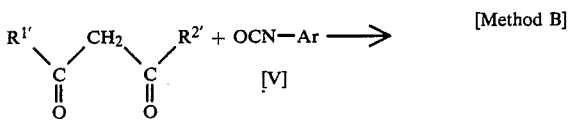

[Method B]

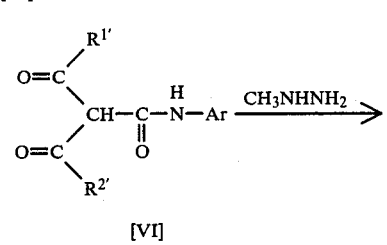

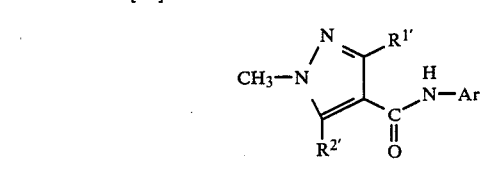

wherein Ar is as defined above and R¹' and R²' which are identical or different represent a methyl group or an ethyl group.

That is, firstly a diketone represented by the formula [IV] is reacted with an isocyanate represented by the formula [V] to obtain a carbamoyl diketone represented by the formula [VI], which is then reacted with methylhydrazine to obtain the present compound.

Reaction solvent is not essential for the reaction of the diketone represented by the formula [IV] with the isocyanate represented by the formula [V], but ordinarily inert solvents are used.

As examples of the solvents, the following are listed; hydrocarbons such as benzene, toluene, etc., halogenated hydrocarbons such as chloroform, dichloromethane, chlorobenzene, etc., ethers such as diethyl ether, diisopropyl ether, tetrahydrofuran, dioxane, dimethoxyethane, etc., ketones such as acetone, methyl isobutyl ketone, etc., nitriles such as acetonitrile, etc., dimethyl sulfoxide, sulfolane, dimethylformamide, dimethylacetamide, etc. and mixtures thereof.

Organic bases such as triethylamine, pyridine, etc., inorganic bases such as sodium hydride, potassium carbonate, etc. and the like may be used as a reaction assistant in this reaction.

Reaction temperature has no special limitation, but the object can be sufficiently achieved by employing the range of 0° C.-100° C.

Amount of the starting compounds used in this reaction is usually 0.7–1.3 mol of the isocyanate represented by the formula [V] per 1 mol of the diketone represented by the formula [IV].

Solvent is not essential for the reaction of thus obtained carbamoyl diketone represented by the formula [VI] with methylhydrazine, but normally inert solvent is used. As examples of the solvent, the following may be listed; hydrocarbons such as benzene, toluene, etc., ethers such as diethyl ether, diisopropyl ether, tetrahydrofuran, dimethoxyethane, etc., alcohols such as methyl alcohol, ethyl alcohol, isopropyl alcohol, etc., water, and the like and mixtures thereof.

Reaction temperature has no special limitation, but generally is 0° C.-100° C. or up to the boiling point of the solvent used.

Amount of the reactant compounds used in this reaction is usually 0.9–1.5 mol of methylhydrazine per 1 mol of the carbamoyldiketone represented by the formula [VI].

[Method C]

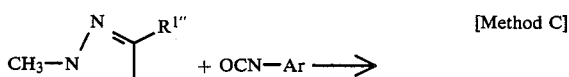

[VIII]

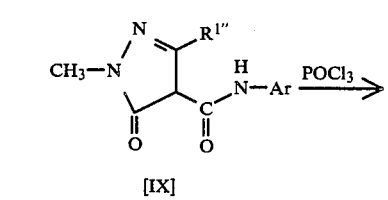

[IX]

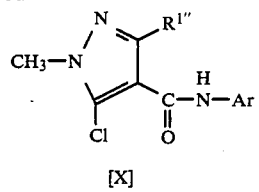

[X]

wherein Ar is as defined above and R¹'' represents a methyl group, an ethyl group or a trifluoromethyl group.

That is, firstly a pyrazoline-5-one represented by the formula [VIII] is reacted with an isocyanate represented by the formula [V] to obtain a 4-carbamoyl-pyrazoline-5-one represented by the formula [IX], which is then reacted with phosphorus oxychloride to obtain a chlorine-substituted pyrazolecarboxamide compound represented by the formula [X].

Solvent is not essential for the reaction of pyrazoline-5-one represented by the formula [VIII] with isocyanate represented by the formula [V], but normally inert solvent is used. As examples of the solvent, the following may be listed; hydrocarbons such as benzene, toluene, etc., halogenated hydrocarbons such as chloroform, dichloromethane, chlorobenzene, etc., ethers such as diethyl ether, diisopropyl ether, tetrahydrofuran, dioxane, dimethoxyethane, etc., ketones such as acetone, methyl isobutyl ketone, etc., nitriles such as acetonitrile, etc., dimethyl sulfoxide, sulfolane, dimethylformamide, dimethylacetamide, etc. and mixtures thereof. Furthermore, organic bases such as triethylamine, pyridine, etc. and inorganic bases such as sodium hydride, potassium carbonate, etc. may also be used as a reaction assistant in this reaction.

Reaction temperature has no special limitation, but usually the object can be sufficiently achieved by employing a temperature of 0° C.-100° C.

Amount of the starting compounds used in this reaction is usually 0.7–1.3 mol of the isocyanate represented by the formula [V] per 1 mol of the pyrazoline-5-one represented by the formula [VIII].

Normally solvent is not necessary for the subsequent reaction of thus obtained carbamoyl pyrazoline-5-one represented by the formula [IX] with phosphorus oxychloride, but inert solvent may be used. As examples of the solvent there are hydrocarbons such as benzene, toluene, etc., halogenated hydrocarbons such as chloroform, dichloromethane, chlorobenzene, etc., ethers such as diethyl ether, diisopropyl ether, tetrahydrofuran, dioxane, dimethoxyethane, etc. Furthermore, an acid accepting agent such as N,N-dimethylaniline, N,N-diethylaniline, 4-dimethylaminopyridine, etc. may be used as reaction assistants in this reaction.

Reaction temperature for this reaction has no special limitation, but usually is the range of from room temperature to the reflux temperature of the reaction mixture.

Amount of the reactant compounds used in this reaction is ordinarily 1.0–20 mols, preferably 5.0–10 mols of phosphorus oxychloride per 1 mol of the carbamoyl-pyrazoline-5-one represented by the formula [IX].

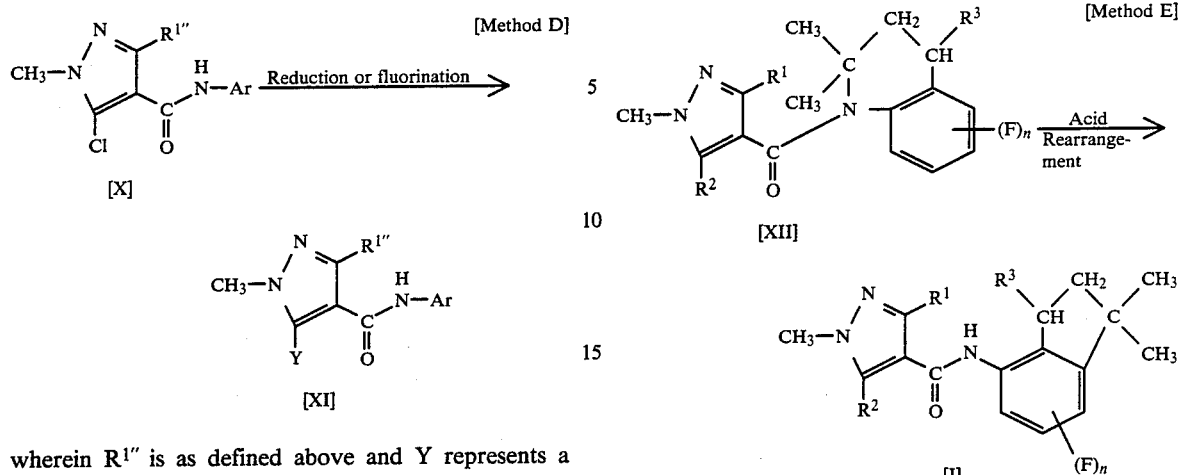

[Method D]

[X]

[XI]

[Method E]

[XII]

[I]

wherein R[1″] is as defined above and Y represents a hydrogen atom or a fluorine atom.

That is, the chlorine-substituted pyrazolecarboxamide compound obtained by [method C] is subjected to reduction reaction to replace a chlorine atom with a hydrogen atom or is subjected to chlorine/fluorine replacing reaction with a fluorinating agent to obtain the pyrazolecarboxamide compound represented by the formula [IX].

The reduction reaction in this method is, for example, a catalytic reduction using a catalyst such as palladium-carbon. Typically the carboxamide compound represented by the formula [X] is subjected to catalytic reduction in hydrocarbons such as benzene, toluene, etc., esters such as ethyl acetate, etc., alcohols such as methyl alcohol, ethyl alcohol, etc. using as a catalyst palladium-carbon (Pd-C) in an amount of 5–50% by weight of the carboxamide compound represented by the formula [X] under a hydrogen pressure of 1–2 atm. in the presence of an acid accepting agent such as anhydrous sodium acetate, anhydrous ammonium acetate or the like.

Fluorinating agents used in the chlorine/fluorine replacing reaction include potassium fluoride, cesium fluoride and the like. Amount of the fluorinating agent is usually 1.0–5.0 mols per 1 mol of the chlorine-substituted pyrazolecarboxamide compound represented by the formula [X].

Normally, inert solvent is used in this reaction. As examples of the solvent, the following may be listed; hydrocarbons such as toluene, xylene, etc., ethers such as bis(2-methoxyethyl)ether, etc., dimethyl sulfoxide, sulfolane, dimethylformamide, dimethylacetamide, etc. and mixtures thereof.

Reaction temperature is usually 100°–200° C.

As reaction assistants, there may be used calcium fluoride and well-known phase transfer catalyst. As phase transfer catalyst, the following may be illustrated; for example, Crown ether, quaternary ammonium salts such as tetraalkyl ammonium halides, phosphonium salts such as tetraalkylphosphonium halides, etc., which are familiar to the skilled.

wherein $R^1$, $R^2$, $R^3$ and n are as defined above.

That is, a tetrahydroquinoline represented by the formula [XII] is subjected to rearrangement in the presence of an acid catalyst to obtain the pyrazolecarboxamide derivative represented by the formula [I].

In this method, there may be used protonic acid and Lewis acid often used as catalyst in Friedel-Crafts reaction as the acids. Normally, the object can be fully attained by using inorganic acids such as sulfuric acid, phosphoric acid, polyphosphoric acid and the like and use of these acids is very advantageous because they also act as reaction solvents. Furthermore, if necessary, halogenated hydrocarbon type inert solvents such as carbon tetrachloride may also be used. Reaction temperature is usually 0° C.–135° C.

The tetrahydroquinoline represented by the formula [XII] used as a starting compound in this method may be synthesized, for example, by a method similar to the methods described in E. Krövenagel et al "Chem. Ber.", 55, 2309 (1922) and W. H. Cliffe et al "J. Chem. Soc.", (C) 514 (1966).

Examples of the present compounds will be shown below but the present compounds are not of course limited to these examples.

1,3-Dimethyl-N-(1,1-dimethylindane-4-yl)pyrazole-4-carboxamide, 1,5-Dimethyl-N-(1,1-dimethylindane-4-yl)pyrazole-4-carboxamide, 1,3,5-Trimethyl-N-(1,1-dimethylindane-4-yl)pyrazole-4-carboxamide, 1,3-Dimethyl-5-fluoro-N-(1,1-dimethylindane-4-yl)pyrazole-4-carboxamide, 5-Chloro-1,3-dimethyl-N-(1,1-dimethylindane-4-yl)pyrazole-4-carboxamide, 5-Bromo-1,3-dimethyl-N-(1,1-dimethylindane-4-yl)pyrazole-4-carboxamide, 1,3-Dimethyl-5-iodo-N-(1,1-dimethylindane-4-yl)pyrazole-4-carboxamide, 1,5-Dimethyl-3-fluoro-N-(1,1-dimethylindane-4-yl)pyrazole-4-carboxamide, 3-Fluoro-1,5-dimethyl-N-(1,1-dimethylindane-4-yl)pyrazole-4-carboxamide, 3-Chloro-1,5-dimethyl-N-(1,1-dimethylindane-4-yl)pyrazole-4-carboxamide, 3-Bromo-1,5-dimethyl-N-(1,1-dimethylindane-4-yl)pyrazole-4-carboxamide, 1,5-Dimethyl-3-iodo-N-(1,1-dimethylindane-4-yl)pyrazole-4-carboxamide,
3,5-Difluoro-1-methyl-N-(1,1-dimethylindane-4-yl)pyrazole-4-carboxamide,
3,5-Dichloro-1-methyl-N-(1,1-dimethylindane-4-yl)pyrazole-4-carboxamide,
3,5-Dibromo-1-methyl-N-(1,1-dimethylindane-4-yl)pyrazole-4-carboxamide,
3,5-Diiodo-1-methyl-N-(1,1-dimethylindane-4-yl)pyrazole-4-carboxamide,
1-Methyl-3-trifluoromethyl-N-(1,1-dimethylindane-4-yl)pyrazole-4-carboxamide,
1-Methyl-5-trifluoromethyl-N-(1,1-dimethylindane-4-yl)pyrazole-4-carboxamide,
3-Fluoro-1-methyl-5-trifluoromethyl-N-(1,1-dimethylindane-4-yl)pyrazole-4-carboxamide,
5-Fluoro-1-methyl-3-trifluoromethyl-N-(1,1-dimethylindane-4-yl)pyrazole-4-carboxamide,
3-Chloro-1-methyl-5-trifluoromethyl-N-(1,1-dimethylindane-4-yl)pyrazole-4-carboxamide,
5-Chloro-1-methyl-3-trifluoromethyl-N-(1,1-dimethylindane-4-yl)pyrazole-4-carboxamide,
5-Bromo-1-methyl-3-trifluoromethyl-N-(1,1-dimethylindane-4-yl)pyrazole-4-carboxamide,
5-Iodo-1-methyl-3-trifluoromethyl-N-(1,1-dimethylindane-4-yl)pyrazole-4-carboxamide,
1,3-Dimethyl-5-trifluoromethyl-N-(1,1-dimethylindane-4-yl)pyrazole-4-carboxamide,
1,5-Dimethyl-3-trifluoromethyl-N-(1,1-dimethylindane-4-yl)pyrazole-4-carboxamide,
3,5-Bis(trifluoromethyl)-1-methyl-N-(1,1-dimethylindane-4-yl)pyrazole-4-carboxamide,
1,3-Dimethyl-N-(1,1,3-trimethylindane-4-yl)pyrazole-4-carboxamide,
1,5-Dimethyl-N-(1,1,3-trimethylindane-4-yl)pyrazole-4-carboxamide,
1,3,5-Trimethyl-N-(1,1,3-trimethylindane-4-yl)pyrazole-4-carboxamide,
1,5-Dimethyl-3-fluoro-N-(1,1,3-trimethylindane-4-yl)pyrazole-4-carboxamide,
1,3-Dimethyl-5-fluoro-N-(1,1,3-trimethylindane-4-yl)pyrazole-4-carboxamide,
3-Chloro-1,5-dimethyl-N-(1,1,3-trimethylindane-4-yl)pyrazole-4-carboxamide,
5-Chloro-1,3-dimethyl-N-(1,1,3-trimethylindane-4-yl)pyrazole-4-carboxamide,
5-Bromo-1,3-dimethyl-N-(1,1,3-trimethylindane-4-yl)pyrazole-4-carboxamide,
1,3-Dimethyl-5-iodo-N-(1,1,3-trimethylindane-4-yl)pyrazole-4-carboxamide,
3-Bromo-1,5-dimethyl-N-(1,1,3-trimethylindane-4-yl)pyrazole-4-carboxamide,
1,5-Dimethyl-3-iodo-N-(1,1,3-trimethylindane-4-yl)pyrazole-4-carboxamide,
3,5-Difluoro-1-methyl-N-(1,1,3-trimethylindane-4-yl)pyrazole-4-carboxamide,
3,5-Dichloro-1-methyl-N-(1,1,3-trimethylindane-4-yl)pyrazole-4-carboxamide,
3,5-Dibromo-1-methyl-N-(1,1,3-trimethylindane-4-yl)pyrazole-4-carboxamide,
3,5-Diiodo-1-methyl-N-(1,1,3-trimethylindane-4-yl)pyrazole-4-carboxamide,
1-Methyl-3-trifluoromethyl-N-(1,1,3-trimethylindane-4-yl)pyrazole-4-carboxamide,
1-Methyl-5-trifluoromethyl-N-(1,1,3-trimethylindane-4-yl)pyrazole-4-carboxamide,
3-Fluoro-1-methyl-5-trifluoromethyl-N-(1,1,3-trimethylindane-4-yl)pyrazole-4-carboxamide,
5-Fluoro-1-methyl-3-trifluoromethyl-N-(1,1,3-trimethylindane-4-yl)pyrazole-4-carboxamide,
3-Chloro-1-methyl-5-trifluoromethyl-N-(1,1,3-trimethylindane-4-yl)pyrazole-4-carboxamide,
5-Chloro-1-methyl-3-trifluoromethyl-N-(1,1,3-trimethylindane-4-yl)pyrazole-4-carboxamide,
5-Bromo-1-methyl-3-trifluoromethyl-N-(1,1,3-trimethylindane-4-yl)pyrazole-4-carboxamide,
5-Iodo-1-methyl-3-trifluoromethyl-N-(1,1,3-trimethylindane-4-yl)pyrazole-4-carboxamide,
1,3-Dimethyl-5-trifluoromethyl-N-(1,1,3-trimethylindane-4-yl)pyrazole-4-carboxamide,
1,5-Dimethyl-3-trifluoromethyl-N-(1,1,3-trimethylindane-4-yl)pyrazole-4-carboxamide,
3,5-Bis(trifluoromethyl)-1-methyl-N-(1,1,3-trimethylindane-4-yl)pyrazole-4-carboxamide,
3-Ethyl-1-methyl-N-(1,1-dimethylindane-4-yl)pyrazole-4-carboxamide,
5-Ethyl-1-methyl-N-(1,1-dimethylindane-4-yl)pyrazole-4-carboxamide,
3-Ethyl-1-methyl-N-(1,1,3-trimethylindane-4-yl)pyrazole-4-carboxamide,
5-Ethyl-1-methyl-N-(1,1,3-trimethylindane-4-yl)pyrazole-4-carboxamide,
1,3-Dimethyl-5-ethyl-N-(1,1-dimethylindane-4-yl)pyrazole-4-carboxamide,
1,3-Dimethyl-5-ethyl-N-(1,1,3-trimethylindane-4-yl)pyrazole-4-carboxamide,
1,5-Dimethyl-3-ethyl-N-(1,1-dimethylindane-4-yl)pyrazole-4-carboxamide,
1,5-Dimethyl-3-ethyl-N-(1,1,3-trimethylindane-4-yl)pyrazole-4-carboxamide,
3-Ethyl-5-fluoro-1-methyl-N-(1,1-dimethylindane-4-yl)pyrazole-4-carboxamide,
5-Ethyl-3-fluoro-1-methyl-N-(1,1-dimethylindane-4-yl)pyrazole-4-carboxamide,
3-Ethyl-5-fluoro-1-methyl-N-(1,1,3-trimethylindane-4-yl)pyrazole-4-carboxamide,
5-Ethyl-3-fluoro-1-methyl-N-(1,1,3-trimethylindane-4-yl)pyrazole-4-carboxamide,
5-Chloro-3-ethyl-1-methyl-N-(1,1-dimethylindane-4-yl)pyrazole-4-carboxamide,
3-Chloro-5-ethyl-1-methyl-N-(1,1-dimethylindane-4-yl)pyrazole-4-carboxamide,
5-Chloro-3-ethyl-1-methyl-N-(1,1,3-trimethylindane-4-yl)pyrazole-4-carboxamide,
3-Chloro-5-ethyl-1-methyl-N-(1,1,3-trimethylindane-4-yl)pyrazole-4-carboxamide,
5-Bromo-3-ethyl-1-methyl-N-(1,1-dimethylindane-4-yl)pyrazole-4-carboxamide,
3-Bromo-5-ethyl-1-methyl-N-(1,1-dimethylindane-4-yl)pyrazole-4-carboxamide,
5-Bromo-3-ethyl-1-methyl-N-(1,1,3-trimethylindane-4-yl)pyrazole-4-carboxamide,
3-Bromo-5-ethyl-1-methyl-N-(1,1,3-trimethylindane-4-yl)pyrazole-4-carboxamide,
3-Ethyl-5-iodo-1-methyl-N-(1,1-dimethylindane-4-yl)pyrazole-4-carboxamide,
5-Ethyl-3-iodo-1-methyl-N-(1,1-dimethylindane-4-yl)pyrazole-4-carboxamide,
3-Ethyl-5-iodo-1-methyl-N-(1,1,3-trimethylindane-4-yl)pyrazole-4-carboxamide,
5-Ethyl-3-iodo-1-methyl-N-(1,1,3-trimethylindane-4-yl)pyrazole-4-carboxamide,
3-Ethyl-1-methyl-5-trifluoromethyl-N-(1,1-dimethylindane-4-yl)pyrazole-4-carboxamide,
5-Ethyl-1-methyl-3-trifluoromethyl-N-(1,1-dimethylindane-4-yl)pyrazole-4-carboxamide, 3-Ethyl-1-methyl-5-trifluoromethyl-N-(1,1,3-trimethyl-indane-4-yl)pyrazole-4-carboxamide,
5-Ethyl-1-methyl-3-trifluoromethyl-N-(1,1,3-trimethyl-indane-4-yl)pyrazole-4-carboxamide,
1,3,5-trimethyl-N-(1,1-dimethyl-5-fluoroindane-4-yl)pyrazole-4-carboxamide,
5-Chloro-1,3-dimethyl-N-(1,1-dimethyl-5-fluoroindane-4-yl)pyrazole-4-carboxamide,
1,3-Dimethyl-5-fluoro-N-(1,1-dimethyl-5-fluoroindane-4-yl)pyrazole-4-carboxamide,
1,5-Dimethyl-3-trifluoromethyl-N-(1,1-dimethyl-5-fluoroindane-4-yl)pyrazole-4-carboxamide,
1,3,5-Trimethyl-N-(1,1-dimethyl-7-fluoroindane-4-yl)pyrazole-4-carboxamide,
5-Chloro-1,3-dimethyl-N-(1,1-dimethyl-7-fluoroindane-4-yl)pyrazole-4-carboxamide,
1,3-Dimethyl-5-fluoro-N-(1,1-dimethyl-7-fluoroindane-4-yl)pyrazole-4-carboxamide,
1,5-Dimethyl-3-trifluoromethyl-N-(1,1-dimethyl-7-fluoroindane-4-yl)pyrazole-4-carboxamide, Production of the present compounds will be explained by the following synthesis examples.

SYNTHESIS EXAMPLE 1

[Synthesis of compound (6)]

To a solution of 1.61 g of 1,1-dimethyl-4-aminoindane and 2 ml of pyridine in 50 ml of toluene was added drop by drop with stirring at room temperature a solution of 2.47 g of 5-chloro-1-methyl-3-trifluoromethylpyrazole-4-carboxylic acid chloride in 10 ml of toluene, followed by stirring at room temperature for 12 hours. Thereafter, the reaction solution was poured into a cold water to result in separation into two layers. The aqueous layer was extracted with ethyl acetate. The resultant organic layer was dried over anhydrous magnesium sulfate and the solvent was distilled off. The residue was recrystallized using toluene to obtain 3.01 g of 5-chloro-1-methyl-3-trifluoromethyl-N-(1,1-dimethylindane-4-yl)pyrazole-4-carboxamide having a melting point of 119.9° C.

SYNTHESIS EXAMPLE 2

[Synthesis of compound (1)]

To a solution of 600 mg (6.0 mmol) of acetylacetone and 1.12 g (6.0 mmol) of 1,1-dimethylindane-4-yl isocyanate in 10 ml of toluene was added dropwise 730 mg (7.2 mmol) of triethylamine at room temperature with stirring, followed by further stirring at room temperature for 12 hours. Then the reaction solution was concentrated under reduced pressure to obtain crude 3-(1,1-dimethylindane-4-yl carbamoyl)pentane-2,4-dione. Then, thus obtained crude 3-(1,1-dimethylindane-4-yl carbamoyl)pentane-2,4-dione was dissolved in 10 ml of ethanol. To the solution was added 276 mg (6.0 mmol) of ethylhydrazine, followed by stirring at room temperature for 6 hours and then for further one hour under reflux with heating. After left standing for cooling, the solvent was distilled off under reduced pressure and the residue was recrystallized with methanol to obtain 1.25 g of 1,3,5-trimethyl-N-(1,1-dimethylindane-4-yl)pyrazole-4-carboxamide which had a melting point of 151.6° C.

SYNTHESIS EXAMPLE 3

[Synthesis of compound (2)]

1.12 g (10 mmol) of 1,3-dimethylpyrazoline-5-one was suspended in 10 ml of toluene containing 1.11 g of triethylamine. To the suspension was added dropwise a solution of 1.87 g of 1,1-dimethylindane-4-yl isocyanate in 2 ml of toluene with stirring at room temperature, followed by further stirring at room temperature for 12 hours. Thereafter, the reaction mixture was extracted with water three times. The aqueous layers were made acidic with concentrated hydrochloric acid and cooled with ice. The precipitate produced was filtered and air-dried to obtain 1.81 g of 1,3-dimethyl-5-oxo-N-(1,1-dimethylindane-4-yl)4,5-dihydropyrazole-4-carboxamide (mp 141.4° C.). Then, thus obtained 1,3-dimethyl-5-oxo-N-(1,1-dimethylindane-4-yl)-4,5-dihydropyrazole-4-carboxamide was added to a mixture of 5 ml of phosphorus oxychloride and 907 mg of N,N-diethylaniline. The resultant mixture was stirred under reflux with heating for 1.5 hour. The obtained reaction mixture was poured into ice water and extracted with chloroform three times. The chloroform layer was washed with water and dried over anhydrous magnesium sulfate. Thereafter, the solvent was distilled off under reduced pressure and the residue was recrystallized with ethanol to obtain 0.96 g of 5-chloro-1,3-dimethyl-N-(1,1-dimethylindane-4-yl)pyrazole-4-carboxamide (mp 175.2° C.).

SYNTHESIS EXAMPLE 4

[Synthesis of compound (3)]

270 mg of 5-chloro-1,3-dimethyl-N-(1,1-dimethylindane-4-yl)pyrazole-4-carboxamide obtained in Synthesis Example 1 was dissolved in 6 ml of ethanol and subjected to catalytic reduction using 40 mg of Pd/C (5%) as a catalyst in the presence of 150 mg of anhydrous sodium acetate. After completion of the reaction, the catalyst and a precipitate were filtered off with Celite and the filtrate was concentrated under reduced pressure and the residue was subjected to silica gel column chromatography to obtain 156 mg of 1,3-dimethyl-N-(1,1-dimethyl-indane-4-yl)pyrazole-4-carboxamide (mp 146.8° C.).

SYNTHESIS EXAMPLE 5

[Synthesis of compound (5)]

1.0 g of potassium fluoride powder, 15 ml of sulfolane and 20 ml of toluene were charged in a reactor and water in the reaction system was removed by molecular sieves under reflux with heating, then toluene was distilled off and the content was cooled. Then, thereto was added 318 mg of 5-chloro-1,3-dimethyl-N-(1,1-dimethylindane-4-yl)pyrazole-4-carboxamide and the mixture was heated in a nitrogen atmosphere at 180°-200° C. for 16 hours. After cooling, to the reaction mixture were added water and ether to result in separation into two layers. The aqueous layer was extracted with ether while the ether layer was washed with a saturated aqueous sodium chloride solution and dried over anhydrous magnesium sulfate. Then, the solvent was distilled off and the residue was subjected to silica gel column chromatography to obtain 140 mg of 5-fluoro-1,3-dimethyl-N-(1,1-dimethylindane-4-yl)pyrazole-4-carboxamide (mp 138.5° C.). $^{19}$F-NMR spectrum (Solvent: CDCl$_3$, External standard: CF$_3$CO$_2$H)

48 ppm (in the higher magnetic field side against external standard of CF$_3$CO$_2$H)

SYNTHESIS EXAMPLE 6

[Synthesis of compound (11)]

To a solution of 1.75 g of 1,1,3-trimethyl-4-aminoindane and 2 ml of triethylamine in 50 ml of tetrahydrofuran was with stirring at room temperature added dropwise a solution of 1.73 g of 1,3,5-trimethylpyrazole-4-carboxylic acid chloride in 10 ml of tetrahydrofuran, followed by stirring at room temperature for 12 hours. Then, the reaction solution was poured into a cold water to result in separation into two layers. The aqueous layer was extracted with ethyl acetate and the organic layer was dried over anhydrous magnesium sulfate and the solvent was distilled off. The residue was recrystallized with toluene to obtain 2.55 g of 1,3,5-trimethyl-N-(1,1,3-trimethylindane-4-yl)pyrazole-4-carboxamide (mp 176.2° C.).

SYNTHESIS EXAMPLE 7

[Synthesis of compound (15)]

100 g of potassium fluoride powder, 300 ml of sulfolane, 100 ml of toluene and 5 g of 18-Crown-6 were charged in a reactor and water in the system was removed by molecular sieves under reflux with heating, followed by distilling off of toluene and cooling the residue. Then, thereto was added 42 g of 5-chloro-1,3-dimethyl-N-(1,1,3-trimethylindane-4-yl)pyrazole carboxamide and the mixture was stirred with heating at 180°–200° C. for 10 hours in a nitrogen atmosphere. After cooling, water and ether were added to the reaction mixture to result in separation into two layers. The aqueous layer was extracted with ether and the layer extracted was washed with a saturated aqueous sodium chloride solution and dried over anhydrous magnesium sulfate. Then the solvent was distilled off and the residue was recrystallized with cyclohexane-toluene mixed solvent to obtain 31.5 g of 1,3-dimethyl-5-fluoro-N-(1,1,3-trimethylindane-4-yl)pyrazole-4-carboxamide (mp 136.9° C.).

SYNTHESIS EXAMPLE 8

[Synthesis of compound (11)]

5 cc of 85% aqueous sulfuric acid was added to 0.31 g of N-(1,3,5-trimethylpyrazole-4-yl carbonyl)-2,2,4-trimethyl-1,2,3,4-tetrahydroquinoline at room temperature, followed by stirring at the same temperature for 24 hours. The reaction mixture was poured into ice water. The precipitated crystal was filtered and washed with n-hexane. After being dried, the crystal was recrystallized from n-hexane-ethyl acetate to obtain 0.17 g of the objective 1,3,5-trimethyl-N-(1,1,3-trimethylindane-4-yl)pyrazole-4-carboxamide.

Representative examples of the present compounds which can be produced by these methods are shown in Table 1.

TABLE 1

Compounds represented by the formula:

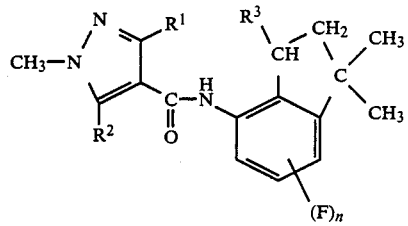

| Compound No. | $R^1$ | $R^2$ | $R^3$ | n | Position of F | Physical constant | $^{19}$F-NMR (ppm)* |
|---|---|---|---|---|---|---|---|
| (1) | $CH_3$ | $CH_3$ | H | 0 | — | mp. 151.6° C. | |
| (2) | $CH_3$ | Cl | H | 0 | — | mp. 175.2° C. | |
| (3) | $CH_3$ | H | H | 0 | — | mp. 146.8° C. | |
| (4) | $CH_3$ | $CH_3$ | H | 1 | 5— | mp. 193.3° C. | |
| (5) | $CH_3$ | F | H | 0 | — | mp. 138.5° C. | 48.0 |
| (6) | $CF_3$ | Cl | H | 0 | — | mp. 119.9° C. | −17.0 |
| (7) | $CF_3$ | $CH_3$ | H | 0 | — | mp. 189.4° C. | −18.5 |
| (8) | $CF_3$ | H | H | 0 | — | mp. 144.1° C. | −18.8 |
| (9) | $CH_3$ | $CF_3$ | H | 0 | — | mp. 139.9° C. | −20.7 |
| (10) | H | $CF_3$ | H | 0 | — | mp. 106.0° C. | −21.0 |
| (11) | $CH_3$ | $CH_3$ | $CH_3$ | 0 | — | mp. 176.2° C. | |
| (12) | $CH_3$ | H | $CH_3$ | 0 | — | mp. 156.2° C. | |
| (13) | H | $CH_3$ | $CH_3$ | 0 | — | mp. 161.0° C. | |
| (14) | $CH_3$ | Cl | $CH_3$ | 0 | — | mp. 134.4° C. | |
| (15) | $CH_3$ | F | $CH_3$ | 0 | — | mp. 136.9° C. | 48.2 |
| (16) | $CF_3$ | $CH_3$ | $CH_3$ | 0 | — | mp. 161.8° C. | −18.3 |
| (17) | $CH_3$ | $CF_3$ | $CH_3$ | 0 | — | mp. 140.3° C. | −20.3 |
| (18) | $CF_3$ | Cl | $CH_3$ | 0 | — | mp. 157.4° C. | −16.9 |
| (19) | $CF_3$ | H | $CH_3$ | 0 | — | mp. 166.2° C. | −18.8 |
| (20) | $C_2H_5$ | $CH_3$ | H | 0 | — | mp. 126.8° C. | |
| (21) | $C_2H_5$ | Cl | H | 0 | — | mp. 140.3° C. | |
| (22) | $C_2H_5$ | F | H | 0 | — | mp. 105.6° C. | 47.8 |
| (23) | $C_2H_5$ | Cl | $CH_3$ | 0 | — | mp. 125.7° C. | |
| (24) | $C_2H_5$ | F | $CH_3$ | 0 | — | mp. 98.3° C. | 48.1 |

*Trifluoroacetic acid was used as an external standard. Negative value indicates lower magnetic field side.

When the present compound is used as an active ingredient of fungicides, it may be used as it is without adding any other components, but generally, it is formulated into emulsifiable concentrates, wettable powders, suspension formulations, granules, dusts, liquids and the like by mixing with a solid or liquid carrier, a surface active agent and other auxiliaries for formulation.

The content of the present compound contained as an active ingredient in these formulations is 0.1 to 99.9%, preferably 0.2 to 80% by weight.

The solid carriers include for example fine powders or granules of kaolin clay, attapulgite clay, bentonite, acid clay, pyrophyllite, talc, diatomaceous earth, calcite, corn starch powder, walnut shell powder, urea, ammonium sulfate, synthetic hydrated silicon dioxide and the like. The liquid carrier includes for example aromatic hydrocarbons such as xylene, methylnaphthalene and the like, alcohols such as isopropanol, ethylene glycol, cellosolve and the like, ketones such as acetone, cyclohexanone, isophorone and the like, vegetable oils such as soybean oil, cotton seed oil and the like, dimethyl sulfoxide, acetonitrile, water and the like.

The surface active agents used for emulsification, dispersion, wetting, etc. include for example anionic surface active agents such as salts of alkyl sulfate, alkyl (aryl) sulfonates, dialkylsulfosuccinates, salts of polyoxyethylene alkylaryl ether phosphoric acid esters, naphthalenesulfonic acid/formalin condensates, etc. and nonionic surface active agents such as polyoxyethylene alkyl ether, polyoxyethylene polyoxypropylene block copolymers, sorbitan fatty acid esters, polyoxyethylene sorbitan fatty acid esters, etc. The auxiliaries for formulation include for example lignosulfonates, alginates, polyvinyl alcohol, gum arabic, CMC (carboxymethyl cellulose), PAP (acid isopropyl phosphate), etc.

The following are formulation examples, where the present compounds used are indicated by the numbers given in Table 1 and parts are by weight.

FORMULATION EXAMPLE 1

Fifty parts of each of the present compounds (1)–(24), 3 parts of calcium lignosulfonate, 2 parts of sodium lauryl sulfate and 45 parts of synthetic hydrated silicon dioxide are thoroughly pulverized and mixed to obtain a wettable powder.

FORMULATION EXAMPLE 2

Ten parts of each of the present compounds (1)–(24), 14 parts of polyoxyethylenestyrylphenyl ether, 6 parts of calcium dodecylbenzenesulfonate and 70 parts of xylene are thoroughly mixed to obtain an emulsifiable concentrate.

FORMULATION EXAMPLE 3

Two parts of each of the present compounds (1)–(24), 1 part of synthetic hydrated silicon dioxide, 2 parts of calcium lignosulfonate, 30 parts of bentonite, and 65 parts of kaolin clay are thoroughly pulverized and mixed, well kneaded with water, then granulated and dried to obtain a granule.

FORMULATION EXAMPLE 4

Twentyfive parts of each of the present compounds (1)–(24), 3 parts of polyoxyethylenesorbitan monooleate, 3 parts of CMC and 69 parts of water are mixed and wet-pulverized to particle size of not more than 5 microns to obtain a suspension formulation.

FORMULATION EXAMPLE 5

Two parts of each of the present compounds (1)–(24), 88 parts of kaolin clay and 10 parts of talc are thoroughly pulverized and mixed to obtain a dust.

These formulations as such or diluted with, for example, water are applied to soil or directly to plants. In more detail, they are used in various forms, e.g., spraying or dusting on plants or spraying, dusting or granule-sprinkling onto soil surface or if necessary, subsequent further soil-mixing.

Fungicidal effects can be expected to be further increased by using them in admixture with other fungicides. Furthermore, these formulations may also be used in admixture with insecticides, acaricides, nematocides, herbicides, plant growth regulating agent, fertilizers, soil improvers and the like.

The present compounds can be used as an active ingredient of fungicides to be used for paddy field, plowland, orchard, pasture, turf and the like.

When the present compound is used as an active ingredient of fungicide, its dosage is generally 0.5 to 100 g, preferably 1 to 50 g per are, although it depends on weather conditions, form of formulations, time, method and place of application, diseases to be controlled, crops to be treated, etc. When the emulsifiable concentrate, wettable powder, suspension forulation, liquid formulation, etc. are diluted with water for use, the concentration is 0.001% to 1%, preferably 0.005% to 0.5%. Granule and dust are used as they are without dilution.

The effect of the present compounds as an active ingredient of fungicides will be shown by the following test examples. The present compounds used are indicated by the compound number given in Table 1 and the compounds used for comparison are indicated by the compounds given in Table 2.

TABLE 2

| Compounds | Chemical formula | Note |
| --- | --- | --- |
| A | ![structure with CH3, OC3H7(i), CNH, O] | Commercially available fungicide mepronil |
| B | $CCl_3-CH-NHCHO$ piperazine ring $CCl_3-CH-NHCHO$ | Commercially available fungicide triforine |
| C | tetrachloroisophthalonitrile (Cl, CN, Cl, CN, Cl, Cl) | Commercially available fungicide TPN |
| D | $Cl-C_6H_4-O-CH(-N\text{-triazole})-C(=O)-C(CH_3)_3$ | Commercially available fungicide triadimefon |

TEST EXAMPLE 1

Test for preventive controlling effect on sheath blight (*Rhizoctonia solani*) of rice.

Sandy loam was filled in a plastic pot and rice (var.: Kinki No. 33) was sowed and cultivated in a greenhouse for 60 days to grow to seedlings in the 6-7 leaf stages. The test compounds were formulated into emulsifiable concentrates in accordance with the Formulation Example 2 and they were diluted with water to a given concentration. These were foliar-sprayed onto the seedlings to allow them to thoroughly deposit on the leaf surface. After 4 hours from the spraying, the seedlings were inoculated by putting agar piece containing *Rhizoctonia solani*. After inoculation, the seedlings were grown at 28° C. for 4 days under highly humid condition and the controlling effects were observed. The results are shown in Table 3.

The controlling effect is determined by observing with the naked eye the condition of disease of test plants on examination, namely, the degree of fungus colony and infected area of leaf and stem and grading the condition of diseases into the following six steps 0, 1, 2, 3, 4 and 5:

5 ... No infected area and fungus colony are noticed.
4 ... Infected area and fungus colony are noticed in about 10% of leaf and stem.

3 ... Infected area and fungus colony are noticed in about 30% of leaf and stem.
2 ... Infected area and fungus colony are noticed in about 50% of leaf and stem.
1 ... Infected area and fungus colony are noticed in about 70% of leaf and stem.
0 ... Infected area and fungus colony are noticed in more than about 70% and no difference is noticed from the condition of disease when no compound is used.

The above grading is applied to all of the following test examples.

TABLE 3

| Test compounds | Concentration of active ingredient (ppm) | Controlling effect |
| --- | --- | --- |
| (1) | 10 | 5 |
| (2) | 10 | 5 |
| (3) | 10 | 5 |
| (4) | 10 | 5 |
| (5) | 10 | 5 |
| (6) | 10 | 5 |
| (7) | 10 | 5 |
| (8) | 50 | 5 |
| (9) | 50 | 5 |
| (10) | 100 | 5 |
| (11) | 10 | 5 |
| (12) | 10 | 5 |
| (13) | 50 | 5 |
| (14) | 10 | 5 |
| (15) | 10 | 5 |
| (16) | 10 | 5 |
| (17) | 100 | 5 |
| (18) | 10 | 5 |
| (19) | 10 | 5 |
| (20) | 50 | 5 |
| (21) | 50 | 5 |
| (22) | 10 | 5 |
| (23) | 100 | 5 |
| (24) | 10 | 5 |
| A | 100 | 4 |

TEST EXAMPLE 2

Test for systemic controlling effect on sheath blight (*Rhizoctonia solani*) of rice.

Sandy loam was filled in a 130 ml plastic pot and rice (var.: Kinki No. 33) was sowed and cultivated in a greenhouse for 8 weeks to grow to seedlings in the 6-7 leaf stages. The test compounds formulated to emulsifiable concentrates in accordance with Formulation Example 2 and they were diluted with water and drenched in a given amount to the soil. After drench, the seedlings were grown in a green-house for 7 days and inoculated by putting agar piece containing *Rhizoctonia solani*. After inoculation, the seedlings were grown at 28° C. for 4 days under a highly humid condition and the controlling effect was observed. The results are shown in Table 4.

TABLE 4

| Test compounds | Dosage of compound (mg/pot) | Controlling effect |
| --- | --- | --- |
| (1) | 1 | 5 |
| (2) | 1 | 5 |
| (3) | 1 | 5 |
| (5) | 1 | 5 |
| (7) | 1 | 5 |
| (11) | 1 | 5 |
| (12) | 1 | 5 |
| (13) | 1 | 5 |
| (14) | 1 | 5 |
| (15) | 1 | 5 |
| (16) | 1 | 5 |

TABLE 4-continued

| Test compounds | Dosage of compound (mg/pot) | Controlling effect |
| --- | --- | --- |
| (19) | 1 | 5 |
| (20) | 1 | 5 |
| A | 1 | 2 |

TEST EXAMPLE 3

Controlling effect on sheath blight (*Rhizoctonia solani*) of rice by submerged application Sandy loam was filled in a 1/10000 a Wagner's pot and rice (var.: Kinki No. 33) was sowed and cultivated in a greenhouse for 80 days to grow to seedlings of the 9-10 leaf stages. The test compounds were formulated into wettable powders in accordance with Formulation Example 1 and diluted with water and drenched in a given amount to the soil. After drench, the seedlings were grown for 7 days in a greenhouse and inoculated by putting agar piece containing *Rhizoctonia solani*. After inoculation, the seedlings were grown at 28° C. for 4 days under a highly humid condition and controlling effect was observed. The results are shown in Table 5.

TABLE 5

| Test compounds | Dosage of active ingredient (g/10a) | Controlling effect |
| --- | --- | --- |
| (6) | 100 | 5 |
| (7) | 100 | 5 |
| (11) | 100 | 5 |
| (12) | 100 | 5 |
| (13) | 100 | 5 |
| (14) | 100 | 5 |
| (15) | 100 | 5 |
| (16) | 100 | 5 |
| (19) | 100 | 5 |
| A | 100 | 3 |

TEST EXAMPLE 4

Test for curative controlling effect on brown rust (*Puccinia recondita*) of wheat Sandy loam was filled in a plastic pot and wheat (var.: Norin No. 73) was sowed and grown in a greenhouse for 10 days to seedlings of the 2-3 leaf stages, which were inoculated with *Puccinia recondita* by dusting. After inoculation, the seedlings were grown at 23° C. for one day under a highly humid condition and onto these seedlings was foliar-sprayed the test compound formulated to wettable powder in accordance with Formulation Example 1 and diluted with water to a given concentration, so that the compound was thoroughly deposited on the leaf surface. After spraying, the seedlings were cultivated at 23° C. for 7 days under illumination and the controlling effect was observed. The results are shown in Table 6.

TABLE 6

| Test compounds | Concentration of active ingredient (ppm) | Controlling effect |
| --- | --- | --- |
| (1) | 1 | 5 |
| (2) | 1 | 5 |
| (3) | 1 | 5 |
| (5) | 1 | 5 |
| D | 1 | 0 |

TEST EXAMPLE 5

Test for curative controlling effect on brown rust (*Puccinia recondita*) of wheat Sandy loam was filled in a plastic pot and wheat (var.: Norin No. 73) was sowed and grown in a greenhouse for 10 days to seedlings of the 2–3 leaf stages, which were inoculated with *Puccinia recondita* by dusting. After inoculation, the seedlings were grown at 23° C. for one day under a highly humid condition and onto these seedlings was foliar-sprayed the test compound formulated to emulsifiable concentrate in accordance with Formulation Example 2 and diluted with water to a given concentration, so that the compound was thoroughly deposited on the leaf surface. After spraying, the seedlings were grown at 23° C. for 7 days under illumination and the controlling effect was examined. The results are shown in Table 7.

TABLE 7

| Test compounds | Concentration of active ingredient (ppm) | Controlling effect |
| --- | --- | --- |
| (8) | 50 | 5 |
|  | 25 | 5 |
|  | 12.5 | 5 |
|  | 6.3 | 5 |
| (11) | 50 | 5 |
|  | 25 | 5 |
|  | 12.5 | 5 |
|  | 6.3 | 5 |
| (14) | 50 | 5 |
|  | 25 | 5 |
| (17) | 50 | 5 |
|  | 25 | 5 |
|  | 12.5 | 5 |
|  | 6.3 | 5 |
| (18) | 50 | 5 |
|  | 25 | 5 |
|  | 12.5 | 5 |
|  | 6.3 | 5 |
| (19) | 50 | 5 |
|  | 25 | 5 |
|  | 12.5 | 5 |
|  | 6.3 | 5 |
| B | 200 | 4 |
|  | 100 | 3 |
|  | 50 | 0 |
|  | 25 | 0 |

TEST EXAMPLE 6

Test for controlling effect on southern blight (*Corticium rolfsii*) of kidney bean.

Sandy loam well mixed with *Corticium rolfsii* which was previously cultured in bran medium was filled in a 250 ml plastic pot and kidney bean (var.: Taishokintoki) was sowed. The test compound was formulated into a wettable powder and diluted with water. A given amount of the test compound was drenched into the soil. After the drench, cultivation was made for 3 weeks in a greenhouse and controlling effect was examined by observing the degree of disease of the stem in the vicinity of the soil surface. The results are shown in Table 8.

TABLE 8

| Test compounds | Dosage of active ingredient (mg/pot) | Controlling effect |
| --- | --- | --- |
| (1) | 1 | 5 |
| (2) | 1 | 5 |
| (3) | 1 | 5 |
| (5) | 1 | 5 |

TABLE 8-continued

| Test compounds | Dosage of active ingredient (mg/pot) | Controlling effect |
| --- | --- | --- |
| A | 1 | 3 |

TEST EXAMPLE 7

Test for preventive controlling effect on scab (*Venturia inaequalis*) of apple

Sandy loam was filled in a plastic pot and seed of apple was sowed and cultivated in a greenhouse for 30 days. Onto the seedlings of the 5 leaf stage was foliar-sprayed the test compound formulated into a wettable powder in accordance with Formulation Example 1 and diluted with water to a given concentration so that the test compound was thoroughly deposited on the leaf surface. After 4 hours from the spraying, the seedlings were inoculated by spraying a suspension of spores of *Venturia inaequalis*. After inoculation the seedlings were grown at 15° C. for 14 days under a highly humid condition and the controlling effect was observed. The results are shown in Table 9.

TABLE 9

| Test compounds | Concentration of Active ingredient (ppm) | Controlling effect |
| --- | --- | --- |
| (8) | 500 | 5 |
| (11) | 500 | 5 |
| (18) | 500 | 5 |
| (19) | 500 | 5 |
| C | 500 | 4 |

What is claimed is:

1. A pyrazolecarboxamide derivative represented by the formula (I):

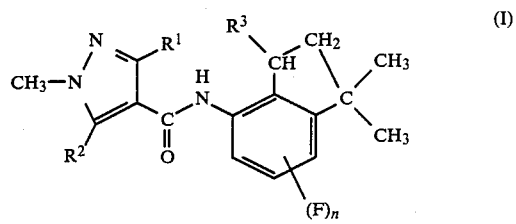

wherein $R^1$ and $R^2$ which are identical or different represent each a hydrogen atom, a halogen atom, a methyl group, an ethyl group or a trifluoromethyl group, $R^3$ represents a hydrogen atom or a methyl group and n represents 0 or 1.

2. A pyrazolecarboxamide derivative according to claim 1, wherein, in the formula (I), $R^1$ is a methyl group or a trifluoromethyl group and $R^2$ is a hydrogen atom, a halogen atom, a methyl group or a trifluoromethyl group.

3. A pyrazolecarboxamide derivative according to claim 1, wherein, in the formula (I), $R^1$ is a methyl group or a trifluoromethyl group and $R^2$ is a hydrogen atom, a fluorine atom, a chlorine atom or a methyl group.

4. A pyrazolecarboxamide derivative according to claim 1, wherein, in the formula (I), $R^1$ is a methyl group or a trifluoromethyl group and $R^2$ is a fluorine atom or a methyl group.

5. A pyrazolecarboxamide derivative according to claim 1, wherein, in the formula (I), $R^1$ is a methyl group or a trifluoromethyl group, $R^2$ is a fluorine atom or a methyl group and n is 0.

6. A pyrazolecarboxamide derivative according to claim 1, wherein, in the formula (I), $R^1$ and $R^2$ each is a methyl group, $R^3$ is a hydrogen atom and n is 0.

7. A pyrazolecarboxamide derivative according to claim 1, wherein, in the formula (I), $R^1$ is a methyl group, $R^2$ is a fluorine atom, $R^3$ is a hydrogen atom and n is 0.

8. A pyrazolecarboxamide derivative according to claim 1, wherein, in the formula (I), $R^1$ is a trifluoromethyl group, $R^2$ is a methyl group, $R^3$ is a hydrogen atom and n is 0.

9. A pyrazolecarboxamide derivative according to claim 1, wherein, in the formula (I), $R^1$, $R^2$ and $R^3$ each is a methyl group and n is 0.

10. A pyrazolecarboxamide derivative according to claim 1, wherein, in the formula (I), $R^1$ and $R^3$ each is a methyl group, $R^2$ is a fluorine atom and n is 0.

11. A pyrazolecarboxamide derivative according to claim 1, wherein, in the formula (I), $R^1$ is a trifluoromethyl group, $R^2$ is a hydrogen atom, $R^3$ is a methyl group and n is 0.

12. A pyrazolecarboxamide derivative according to claim 1, wherein, in the formula (I), $R^1$ and $R^3$ each is a methyl group, $R^2$ is a hydrogen atom and n is 0.

13. A fungicidal composition which comprises as an active ingredient a fungicidally effective amount of a pyrazolecarboxamide derivative represented by the formula (I)

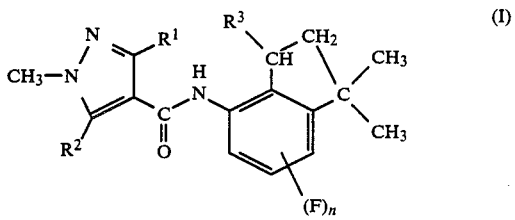

wherein $R^1$ and $R^2$ which are identical or different represent each a hydrogen atom, a halogen atom, a methyl group, an ethyl group or a trifluoromethyl group, $R^3$ represents a hydrogen atom or a methyl group and n represents 0 to 1, and an inert carrier.

14. A fungicidal composition according to claim 13, wherein, in the formula (I), $R^1$ is a methyl group or a trifluoromethyl group and $R^2$ is a hydrogen atom, a fluorine atom, a chlorine atom or a methyl group.

15. A fungicide according to claim 13, wherein, in the formula (I), $R^1$ is a methyl group or a trifluoromethyl group and $R^2$ is a fluorine atom or a methyl group and n is 0.

* * * * *

UNITED STATES PATENT AND TRADEMARK OFFICE
CERTIFICATE OF CORRECTION

PATENT NO. : 4,742,074

DATED : May 3, 1988

INVENTOR(S) : SUMIO NISHIDA, et al.

It is certified that error appears in the above-indentified patent and that said Letters Patent is hereby corrected as shown below:

On title page, left-hand column, item 30,

"Oct. 29, 1985" should be -- Oct. 29, 1984 --.

Signed and Sealed this

Second Day of May, 1995

Attest:

BRUCE LEHMAN

Attesting Officer        Commissioner of Patents and Trademarks